US00PP17673P2

(12) United States Plant Patent
Hambali

(10) Patent No.: US PP17,673 P2
(45) Date of Patent: May 1, 2007

(54) ***AGLAONEMA* PLANT NAMED 'TWYAG0003'**

(50) Latin Name: ***Aglaonema commutatum* × *Aglaonema rotundum***
Varietal Denomination: TWYAG0003

(75) Inventor: Gregori G. Hambali, Bogor (ID)

(73) Assignee: Twyford International, Inc., Apopka, FL (US)

( * ) Notice: Subject to any disclaimer, the term of this patent is extended or adjusted under 35 U.S.C. 154(b) by 0 days.

(21) Appl. No.: 11/230,745

(22) Filed: Sep. 20, 2005

(51) Int. Cl.
*A01H 5/00* (2006.01)

(52) U.S. Cl. ..... Plt./376

(58) Field of Classification Search ..... Plt./376
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Aglaonema* plant named 'TWYAG0003', characterized by its upright and outwardly arching plant form; vigorous growth habit; freely clumping habit; full, dense and bushy appearance; leaf surfaces green in color with pink-colored midribs and random spots and blotches; and pink-colored leaf petioles.

2 Drawing Sheets

Botanical designation: *Aglaonema commutatum*× *Aglaonema rotundum.*
Cultivar denomination: 'TWYAG0003'.

BACKGROUND OF THE INVENTION

The present Invention relates to a new and distinct cultivar of *Aglaonema* plant, botanically known as *Aglaonema commutatum*×*Aglaonema rotundum* and hereinafter referred to by the name 'TWYAG0003'.

The new *Aglaonema* is the result of a planned breeding program conducted by the Inventor in Bogor, Indonesia. The objective of the breeding program is to create new fast-growing *Aglaonema* cultivars with freely clumping habit and unique leaf coloration.

The new *Aglaonema* originated from a cross-pollination made by the Inventor in October, 1988 of the *Aglaonema commutatum* cultivar Tricolor, not patented, as the female, or seed, parent with an unnamed selection of *Aglaonema rotundum,* not patented, as the male, or pollen, parent. The new *Aglaonema* was discovered and selected by the Inventor in October, 2001 as a single plant within the progeny of the stated cross-pollination in a controlled environment in Bogor, Indonesia. The new *Aglaonema* was selected on the basis of its plant habit and uniquely colored foliage.

Asexual propagation of the new cultivar by divisions and cuttings since early 2002 in a controlled environment in Bogor, Indonesia, has shown that the unique features of this new *Aglaonema* are stable and reproduced true to type in successive generations.

SUMMARY OF THE INVENTION

The following traits have been repeatedly observed and are determined to be the unique characteristics of 'TWYAG0003'. These characteristics in combination distinguish 'TWYAG0003' as a new and distinct cultivar of *Aglaonema:*

1. Upright and outwardly arching plant form.
2. Vigorous growth habit.

3. Freely clumping habit; full, dense and bushy appearance.
4. Unique leaf coloration; leaf surfaces green in color with pink-colored midribs and random spots and blotches.
5. Pink-colored leaf petioles.

In side-by-side comparisons conducted by the Inventor in Bogor, Indonesia, plants of the new *Aglaonema* differed from plants of the female parent, the cultivar Tricolor, in the following characteristics:

1. Plants of the new *Aglaonema* had broader leaves than plants of the cultivar Tricolor.
2. Plants of the new *Aglaonema* and the cultivar Tricolor differed in leaf and leaf petiole coloration.

In side-by-side comparisons conducted by the Inventor in Bogor, Indonesia, plants of the new *Aglaonema* differed from plants of the male parent selection in the following characteristics:

1. Plants of the new *Aglaonema* were more upright than plants of the male parent selection.
2. Leaves of plants of the new *Aglaonema* were more oblong than leaves of plants of the male parent selection.
3. Plants of the new *Aglaonema* and the male parent selection differed in leaf and leaf petiole coloration.
4. Plants of the new *Aglaonema* were resistant to *Erwinia* whereas plants of the male parent selection were susceptible to *Erwinia.*

Plants of the new *Aglaonema* can be compared to plants of the cultivar Red Gold, not patented. In side-by-side comparisons conducted in Apopka, Fla., plants of the new *Aglaonema* differed from plants of the *Aglaonema* cultivar Red Gold in the following characteristics:

1. Plants of the new *Aglaonema* more upright than plants of the cultivar Red Gold.
2. Leaves of plants of the new *Aglaonema* were narrower than leaves of plants of the cultivar Red Gold.
3. Plants of the new *Aglaonema* and the cultivar Red Gold differed in leaf coloration.

BRIEF DESCRIPTION OF THE PHOTOGRAPHS

The accompanying colored photographs illustrate the overall appearance of the new *Aglaonema,* showing the colors as true as it is reasonably possible to obtain in colored reproductions of this type. Colors in the photographs may differ slightly from the color values cited in the detailed botanical description which accurately describe the colors of the new *Aglaonema.*

The photograph on the first sheet comprises a top perspective view of a typical plant of 'TWYAG0003' grown in a container.

The photographs on the second page are close-up views of upper and lower surfaces of developing leaves (top of sheet) and fully expanded leaves (bottom of sheet) of 'TWYAG0003'.

DETAILED BOTANICAL DESCRIPTION

The cultivar TWYAG0003 has not been observed under all possible environmental conditions. The phenotype may vary somewhat with variations in environment such as temperature and light intensity without, however, any variance in genotype.

The following observations and measurements describe plants of the new *Aglaonema* that were grown in 20-cm containers, in Apopka, Fla., in a polypropylene-covered shadehouse with light levels about 2,500 foot-candles. During the production of the plants, day temperatures were about 27° C. to 29° C. and night temperatures ranged from 14° C. to 25° C. Plants used for the photographs and description were about 16 months from planting. Color references are made to The Royal Horticultural Society Colour Chart, 2001 Edition, except where general terms of ordinary dictionary significance are used.

Botanical classification: *Aglaonema commutatum*× *Aglaonema rotundum* cultivar TWYAG0003.

Parentage:

*Female, or seed, parent.*—*Aglaonema commutatum* cultivar Tricolor, not patented.

*Male, or pollen, parent.*—Unnamed selection of *Aglaonema rotundum,* not patented.

Propagation:

*Type.*—By divisions.

*Time to initiate roots.*—About three weeks.

*Time to produce a rooted plant.*—About four to five weeks.

*Root description.*—Thick, fibrous, fleshy; 19D in color.

*Rooting habit.*—Freely-branching; dense.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 15 to 25-cm containers.

*Growth habit.*—Freely clumping habit; plants typically produce about 18 offshoots per plant; full, dense and bushy appearance.

*Plant height.*—About 27 cm.

*Plant width* (*spread*).—About 55 cm.

*Stem description.*—Length: About 12 cm. Diameter: About 1 cm. Internode length: About 1.2 cm. Aspect: Upright. Strength: Good; flexible. Color, immature: 157B. Color, mature: 162A to 162B.

*Foliage description.*—Arrangement: Alternate; single. Length: About 19 cm. Width: About 9.5 cm. Shape: Elliptic. Apex: Acute. Base: Obtuse. Margin: Entire; mostly flat with some broad undulations. Texture, upper and lower surfaces: Smooth, glabrous; rugose. Veins: Recessed on upper surface and prominent on lower surface. Venation pattern: Pinnate. Color: Developing leaves, upper surface: Alternating chevrons of 191A and darker than 147A; random spots and blotches, 65C; venation, 65B to 65C. Developing leaves, lower surface: Ground color, 147A, flushed with 52B; random spots and blotches from upper surface visible; venation, 52C. Fully expanded leaves, upper surface: Alternating chevrons of 189A and more green than N189A; random spots and blotches, 65B; venation, 54D tinged with 53D. Fully expanded leaves, lower surface: Ground color, darker green than N189A, flushed with 53D; random spots and blotches from upper surface visible; venation, 53C to 53D. Petiole: Aspect: Initially upright; when mature, about 40° from vertical; base, clasping. Length: About 12 cm. Diameter, distal: About 4.5 cm. Diameter, proximal: About 3.1 cm. Color: 55B to 54B. Wing length: About 8 cm. Wing diameter: About 8 mm. Wing color: 65D; flushed with 27D; striations, 53D.

Inflorescence description:

*Inflorescence arrangement/quantity.*—Concave spathes with spadices held beneath the foliar plane; inflorescences arise from leaf axils and sheathed by cataphylls; about two to three inflorescences per plant.

*Time to flower.*—Inflorescences develop during the autumn and winter in Apopka, Fla.; flowering intermittent.

*Inflorescence longevity.*—About 12 to 15 weeks on the plant; inflorescences not persistent.

*Fragrance.*—None detected.

*Cataphylls.*—Length: About 5.1 cm. Diameter: About 7 to 8 mm. Shape: Oblong to elliptic; apex, acute to cuspidate; base, clasping; one to two-keeled. Color: 73D tinged with 73B to 73C along the keel.

*Spathe.*—Length: About 5.5 cm. Width: About 5.4 cm. Shape: Broadly elliptic. Apex: Cuspidate. Base: Cuneate. Margin: Entire. Aspect: Concave, curling over the spadix. Color: When developing, front surface: Mottled, 146C to 146D and 147B to 147C. When developing, rear surface: Mottled, 147B, 146D and 145C. Fully developed, front and rear surfaces: Base color, 155D; random speckles, 145A to 145B; with development, 159D tinged with 160C.

*Spadix.*—Length: About 3.3 cm. Diameter: About 9.5 mm. Shape: Columnar, cylindrical; apex, obtuse. Aspect: Mostly upright. Color: Female zone, when developing: 12C. Male zone, when developing: 155B. Female zone, mature: 144C; stigma, 17D. Male zone, mature: N155D. Quantity of female flowers per spadix: About ten. Quantity of male flowers per spadix: About 250. Flower diameter: About 3 mm. Pollen: None observed.

*Peduncles.*—Length: About 8 cm. Diameter: About 3 mm. Aspect: Upright to slightly outward with development. Strength: Good; flexible. Color: 159C tinged with 145B; faint blotches, tinged with 170D.

*Pedicels.*—Length: About 7 mm. Diameter: About 3.5 mm. Aspect: Upright to about 45° from vertical.

Strength: Good; flexible. Color: 155B to 145B to 145C.

*Fruit/seed.*—Fruit and seed development have not been observed.

Disease/pest resistance: Plants of the new *Aglaonema* have been observed to be resistant to *Erwinia*. Plants of the new *Aglaonema* have not been observed to be resistant to pests and other pathogens common to *Aglaonema*.

Weather tolerance: Plants of the new *Aglaonema* have been observed to be tolerant to wind, rain and temperatures ranging from 4° C. to 40° C.

It is claimed:

1. A new and distinct cultivar of *Aglaonema* plant named 'TWYAG0003', as illustrated and described.

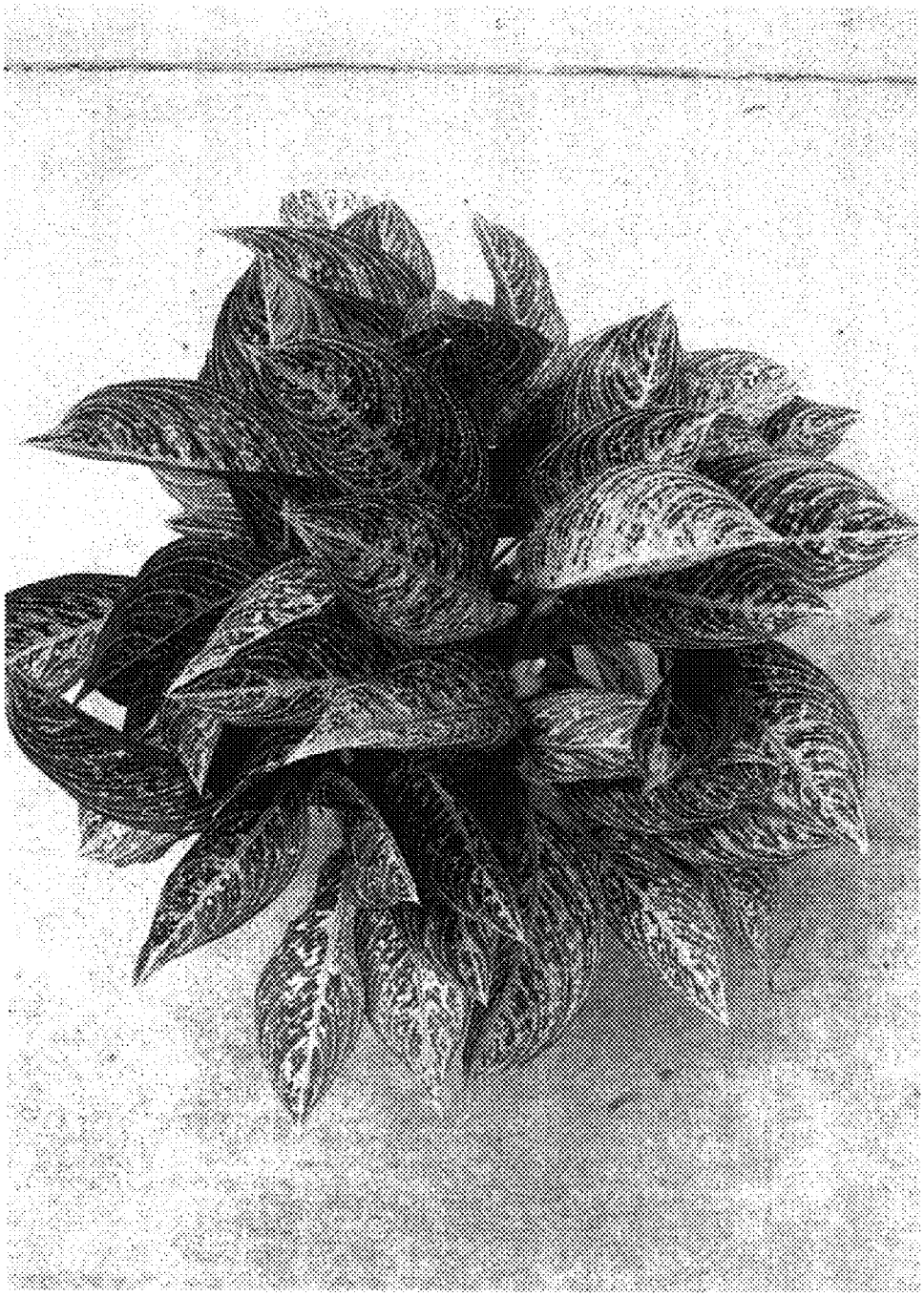

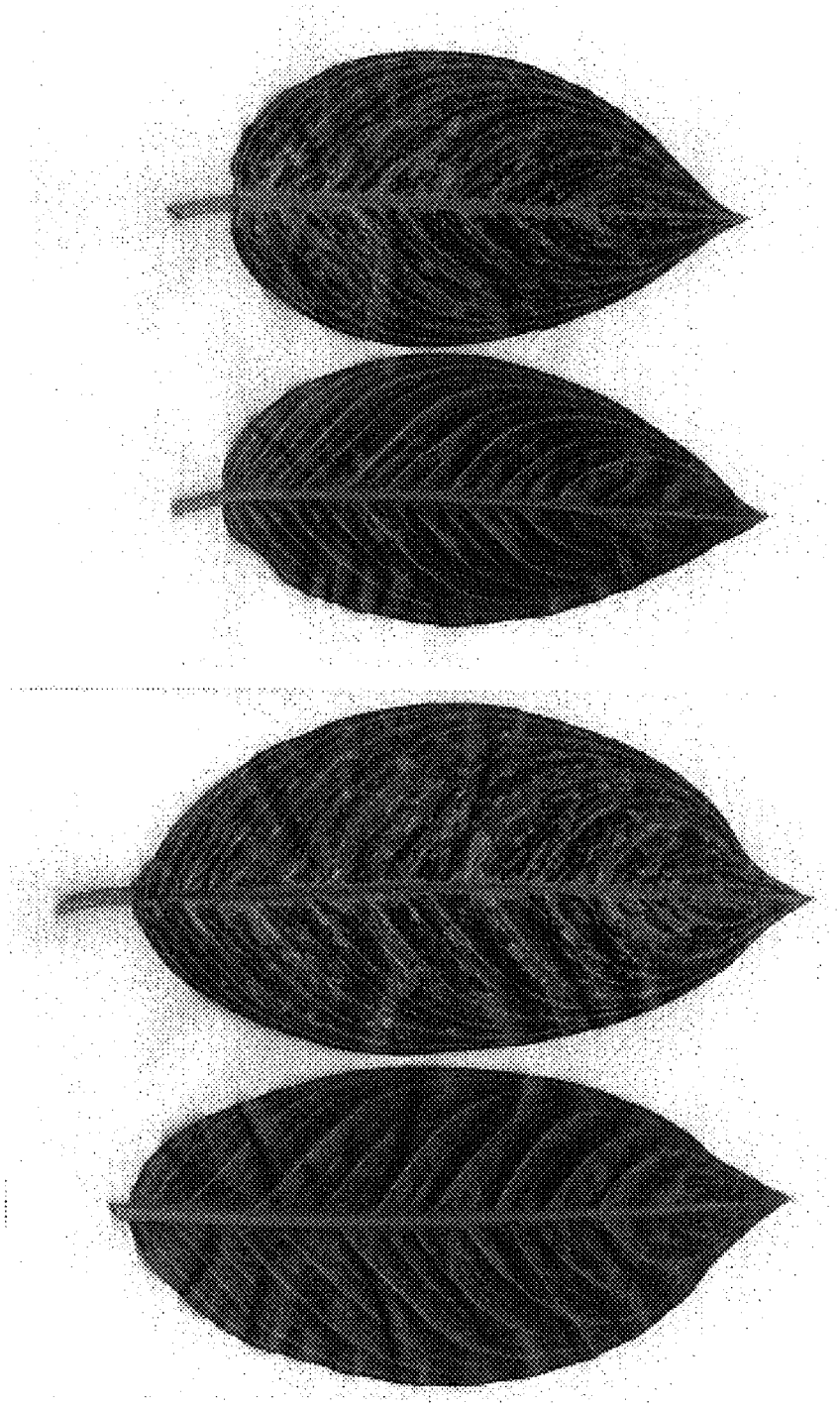

* * * * *